(12) United States Patent
Provencher et al.

(10) Patent No.: US 10,501,235 B2
(45) Date of Patent: Dec. 10, 2019

(54) BIOLOGICAL SAMPLE CONTAINMENT SYSTEM AND LABEL

(71) Applicant: Becton, Dickinson and Company, Franklin Lakes, NJ (US)

(72) Inventors: Eric John Provencher, Edgewater, NJ (US); Craig Owen Russ, Wayne, NJ (US); Bo Yon Lillian Yoo, Ridgefield, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 79 days.

(21) Appl. No.: 14/795,180

(22) Filed: Jul. 9, 2015

(65) Prior Publication Data

US 2016/0016165 A1    Jan. 21, 2016

Related U.S. Application Data

(60) Provisional application No. 62/025,696, filed on Jul. 17, 2014.

(51) Int. Cl.
*B01L 3/00* (2006.01)
*B65D 25/20* (2006.01)
(Continued)

(52) U.S. Cl.
CPC ........ *B65D 25/205* (2013.01); *A61B 5/15003* (2013.01); *A61B 5/150259* (2013.01);
(Continued)

(58) Field of Classification Search
CPC ... B01L 3/5082; B01L 3/5453; B65D 25/205; G09F 3/02; G09F 3/0297; G09F 3/10; A61B 5/14
(Continued)

(56) References Cited

U.S. PATENT DOCUMENTS 4,128,954 A * 12/1978 White .................... B31D 1/027
206/459.5
5,419,591 A    5/1995 Lambert et al.
(Continued)

FOREIGN PATENT DOCUMENTS

| EP | 2 292 331 A2 | 3/2011 |
| EP | 2 571 008 A2 | 3/2013 |

(Continued)

*Primary Examiner* — Jill A Warden
*Assistant Examiner* — Jacqueline Brazin
(74) *Attorney, Agent, or Firm* — The Webb Law Firm

(57) ABSTRACT

A biological sample containment system and a label for a container that includes a first layer having a first readable information portion and a second layer removably attached to the first layer, the second layer having a second readable information portion, is disclosed. In one embodiment, the first layer and the second layer of the label are both formed of a thermosensitive material. In one embodiment, at least a part of the first readable information portion is identical to at least a part of the second readable information portion. The label of the present disclosure allows a portion of the label having readable information to be removed and adhered to a patient record, for example, while a portion of the label having identical readable information remains on the container.

20 Claims, 6 Drawing Sheets

(51) Int. Cl.
*G09F 3/02* (2006.01)
*G09F 3/00* (2006.01)
*G09F 3/10* (2006.01)
*A61B 5/15* (2006.01)
*A61B 5/153* (2006.01)

(52) U.S. Cl.
CPC .. *A61B 5/150755* (2013.01); *A61B 5/150786* (2013.01); *B01L 3/5453* (2013.01); *G09F 3/02* (2013.01); *G09F 3/0297* (2013.01); *G09F 3/10* (2013.01); *A61B 5/153* (2013.01); *B01L 2200/147* (2013.01); *B01L 2300/021* (2013.01); *B01L 2300/0832* (2013.01); *B01L 2300/0887* (2013.01); *G09F 2003/0211* (2013.01); *G09F 2003/0216* (2013.01); *G09F 2003/0219* (2013.01); *G09F 2003/0245* (2013.01); *G09F 2003/0257* (2013.01); *G09F 2003/0272* (2013.01)

(58) Field of Classification Search
USPC .......................................................... 422/549
See application file for complete search history.

(56) References Cited

U.S. PATENT DOCUMENTS

| | | | |
|---|---|---|---|
| 5,642,906 A | 7/1997 | Foote et al. | |
| 5,686,159 A * | 11/1997 | Langan | G09F 3/02 283/81 |
| 5,735,549 A | 4/1998 | Konkol et al. | |
| 5,914,165 A * | 6/1999 | Freedman | B32B 7/06 283/81 |
| 6,130,699 A | 10/2000 | Christensen et al. | |
| 6,133,195 A | 10/2000 | Murphy | |
| 6,135,505 A | 10/2000 | Fendt et al. | |
| 6,280,891 B2 | 8/2001 | Daniel et al. | |
| 6,428,640 B1 * | 8/2002 | Stevens | B65C 9/44 156/215 |
| 6,599,481 B2 * | 7/2003 | Stevens | B01L 3/5453 283/100 |
| 6,637,775 B1 | 10/2003 | Bernier et al. | |
| 6,976,628 B2 | 12/2005 | Krupa | |
| 7,122,157 B2 | 10/2006 | Stevens et al. | |
| 7,407,195 B2 | 8/2008 | Berson | |
| 7,600,684 B2 | 10/2009 | Tobin et al. | |
| 8,228,498 B2 | 7/2012 | Nakahana et al. | |
| 8,287,821 B2 | 10/2012 | Nakahana et al. | |
| 2006/0091669 A1 | 5/2006 | Wilkinson | |
| 2006/0222802 A1 | 10/2006 | Stevens et al. | |
| 2007/0252378 A1 * | 11/2007 | Chambers | G09F 3/0288 283/81 |
| 2008/0121688 A1 * | 5/2008 | Harrop | G06K 19/06028 235/375 |
| 2009/0193696 A1 * | 8/2009 | Golabek, Jr. | B01L 3/5453 40/299.01 |
| 2011/0091669 A1 * | 4/2011 | Tang | A61L 2/232 428/34.1 |
| 2013/0298435 A1 * | 11/2013 | Silvano | G09F 3/0289 40/638 |

FOREIGN PATENT DOCUMENTS

| | | |
|---|---|---|
| JP | 20026743 A | 1/2002 |
| JP | 2007125733 A | 5/2007 |
| JP | 2008518679 A | 6/2008 |
| WO | 2007/092585 A2 | 8/2007 |
| WO | WO 2007/092585 * | 8/2007 |
| WO | 2008/107662 A1 | 9/2008 |
| WO | WO 2008/107662 * | 9/2008 |

* cited by examiner

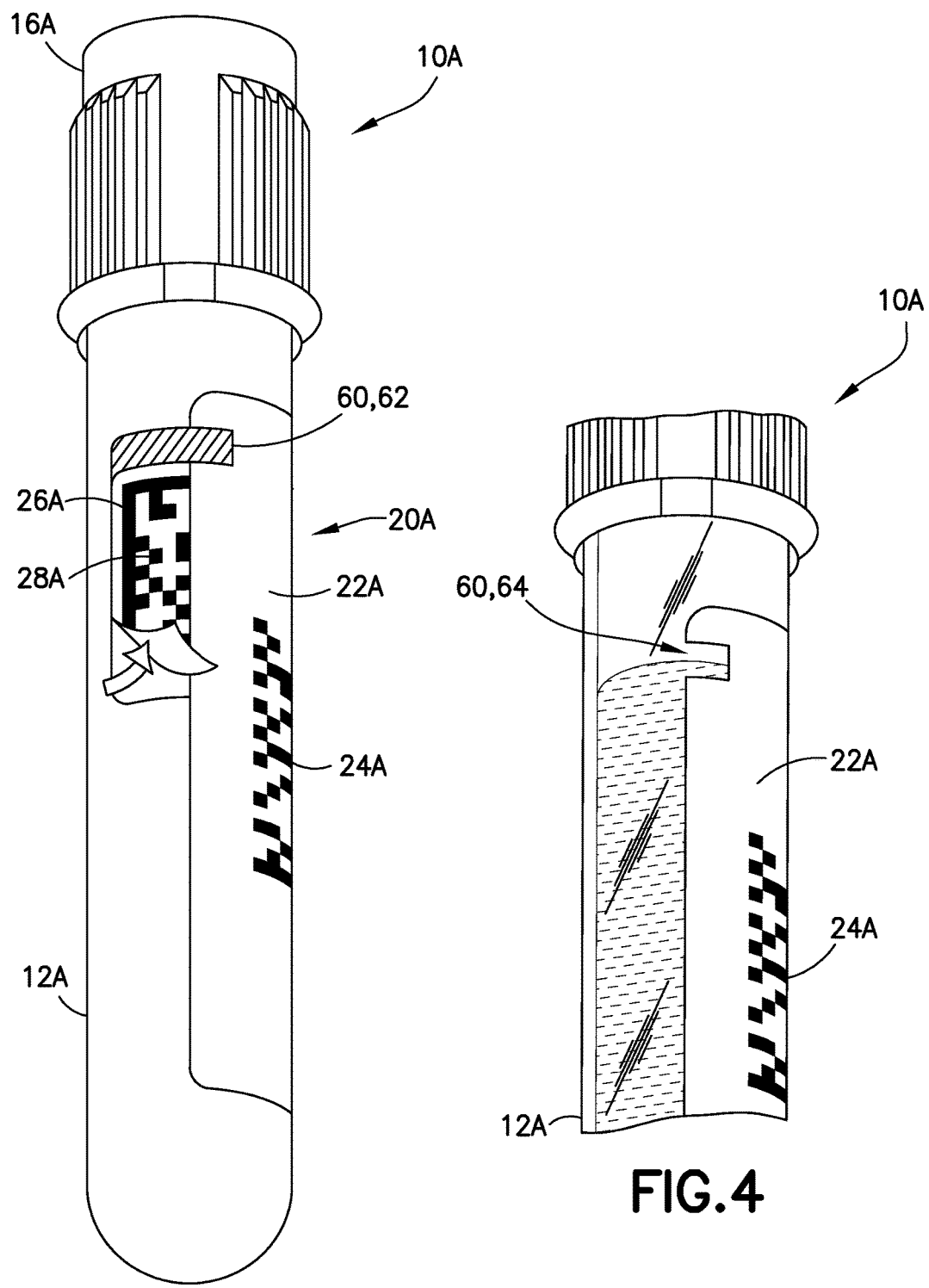

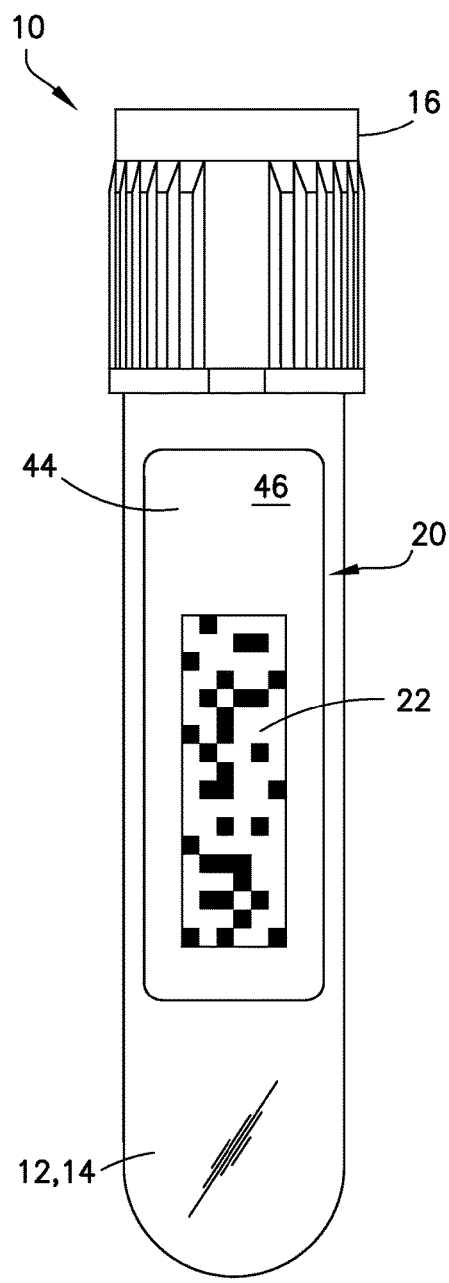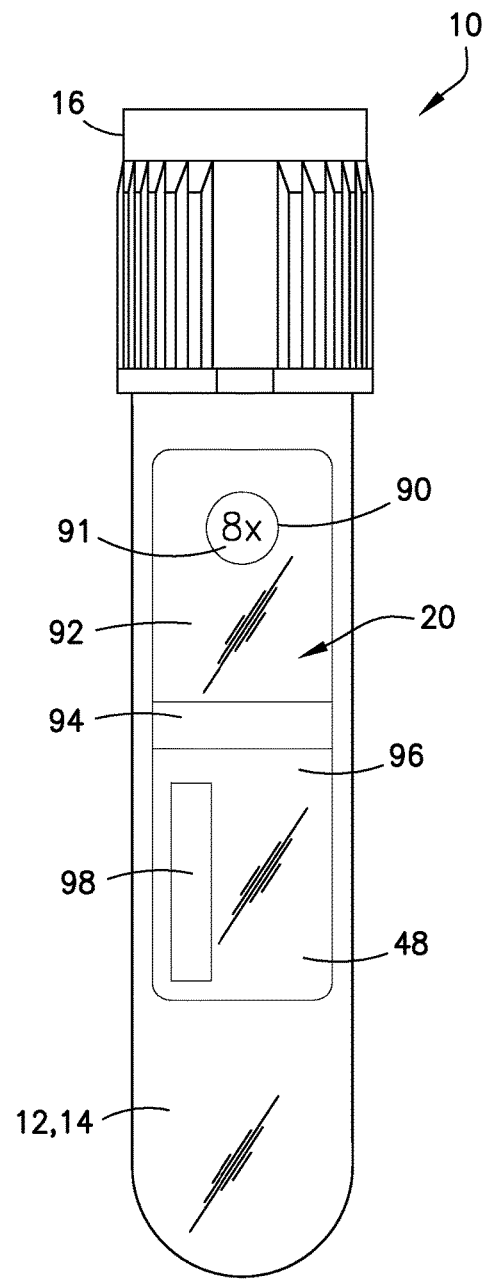

BIOLOGICAL SAMPLE CONTAINMENT SYSTEM AND LABEL

CROSS-REFERENCE TO RELATED APPLICATION

The present application claims priority to U.S. Provisional Application Ser. No. 62/025,696, entitled "Biological Sample Containment System and Label", filed Jul. 17, 2014, the entire disclosure of which is hereby incorporated by reference.

BACKGROUND OF THE INVENTION

1. Field of the Disclosure

The present disclosure relates generally to biological sample containment systems. More particularly, the present disclosure relates to systems and methods for providing identifying information for biological sample containment systems.

2. Description of the Related Art

Biological sample collection containers, such as blood collection containers, are well-known in the medical arts. Biological sample collection containers are used to store a sample obtained by a healthcare professional from a patient until the sample is ready to be tested or used for other purposes.

When collecting biological samples in collection containers, it is often important that the container and/or sample are not exposed to a temperature that exceeds a certain threshold. In addition, it is sometimes important that the container is used within a certain timeframe upon manufacture, shipment, or some other event. In addition, it may be important to know the amount of time that has transpired after collection of the sample into the container.

Additionally, identifying other characteristics and/or information of the sample and/or container may be useful to the healthcare practitioner. For example, identifying the integrity of the sample, whether the sample has been subjected to appropriate procedures, e.g., mixing, or whether the appropriate amount of sample has been collected may be significant.

SUMMARY OF THE INVENTION

The present disclosure provides a biological sample containment system and a label for a container that includes a first layer having a first readable information portion and a second layer removably attached to the first layer, the second layer having a second readable information portion. In one embodiment, the first layer and the second layer of the label are both formed of a thermosensitive material. In one embodiment, at least a part of the first readable information portion is identical to at least a part of the second readable information portion. The label of the present disclosure allows a portion of the label having readable information to be removed and adhered to a patient record, for example, while a portion of the label having identical readable information remains on the container.

In accordance with an embodiment of the present invention, a label for a container includes a first layer having a first readable information portion and formed of a thermosensitive material; and a second layer removably attached to the first layer, the second layer having a second readable information portion and formed of a thermosensitive material.

In one configuration, at least a part of the first readable information portion is identical to at least a part of the second readable information portion. In another configuration, at least a part of the first readable information portion is a first barcode and at least a part of the second readable information portion is a second barcode, the second barcode identical to the first barcode. In yet another configuration, the label includes a securement portion on a surface of the first layer. In one configuration, the securement portion comprises an adhesive on a rear surface of the first layer. In another configuration, at least a part of the first readable information portion and at least a part of the second readable information portion comprise electronically readable information. In yet another configuration, the label includes a release layer disposed between the first layer and the second layer. In one configuration, the label includes a fill line indicator. In another configuration, a portion of the first layer includes the fill line indicator. In yet another configuration, a portion of the second layer includes the fill line indicator. In one configuration, the first layer and the second layer are formed of the same thermosensitive material.

In accordance with another embodiment of the present invention, a biological sample containment system includes a container for collecting a biological sample and a label for the container including a first layer having a first readable information portion and formed of a thermosensitive material and a second layer removably attached to the first layer, the second layer having a second readable information portion and formed of a thermosensitive material.

In one configuration, at least a part of the first readable information portion is identical to at least a part of the second readable information portion. In another configuration, at least a part of the first readable information portion is a first barcode and at least a part of the second readable information portion is a second barcode, the second barcode identical to the first barcode. In yet another configuration, the biological sample containment system includes a securement portion on a surface of the first layer. In one configuration, the securement portion comprises an adhesive on a rear surface of the first layer. In another configuration, at least a part of the first readable information portion and at least a part of the second readable information portion comprise electronically readable information. In yet another configuration, the biological sample containment system includes a release layer disposed between the first layer and the second layer. In one configuration, the label further comprises a fill line indicator. In another configuration, a portion of the first layer includes the fill line indicator. In yet another configuration, a portion of the second layer includes the fill line indicator. In one configuration, the first layer and the second layer are formed of the same thermosensitive material. In yet another configuration, the container is a biological specimen collection container. In one configuration, the container is a blood collection tube.

In accordance with another embodiment of the present invention, a method of providing information on a container includes providing a label comprising a first layer formed of a thermosensitive material and a second layer removably attached to the first layer and formed of a thermosensitive material; providing a container; adhering the label to the container; and imparting a first readable information portion in the first layer and a second readable information portion in the second layer.

In one configuration, the method includes simultaneously imparting the first readable information portion in the first layer and the second readable information portion in the second layer. In another configuration, at least a part of the first readable information portion is identical to at least a part of the second readable information portion. In yet another configuration, at least a part of the first readable information portion is a first barcode and at least a part of the second readable information portion is a second barcode, the second barcode identical to the first barcode. In one configuration, the method includes forming a securement portion on a surface of the first layer. In another configuration, the method includes forming the securement portion on a rear surface of the first layer. In yet another configuration, the securement portion comprises an adhesive. In one configuration, at least a part of the first readable information portion and at least a part of the second readable information portion comprise electronically readable information. In another configuration, the method includes forming a fill line indicator on the label. In yet another configuration, the method includes forming the fill line indicator on a portion of the first layer. In one configuration, the method includes forming the fill line indicator on a portion of the second layer. In another configuration, the first layer and the second layer are formed of the same thermosensitive material.

BRIEF DESCRIPTION OF THE DRAWINGS

The above-mentioned and other features and advantages of this disclosure, and the manner of attaining them, will become more apparent and the disclosure itself will be better understood by reference to the following descriptions of embodiments of the disclosure taken in conjunction with the accompanying drawings, wherein:

FIG. 3 is a perspective view of a biological sample containment system in accordance with another embodiment of the present invention.

FIG. 4 is a fragmentary perspective view of a biological sample containment system in accordance with another embodiment of the present invention.

FIG. 5 is a front elevation view of a biological sample containment system in accordance with an embodiment of the present invention.

FIG. 6 is a rear elevation view of a biological sample containment system in accordance with an embodiment of the present invention.

Corresponding reference characters indicate corresponding parts throughout the several views. The exemplifications set out herein illustrate exemplary embodiments of the disclosure, and such exemplifications are not to be construed as limiting the scope of the disclosure in any manner.

DETAILED DESCRIPTION

Figure 1:
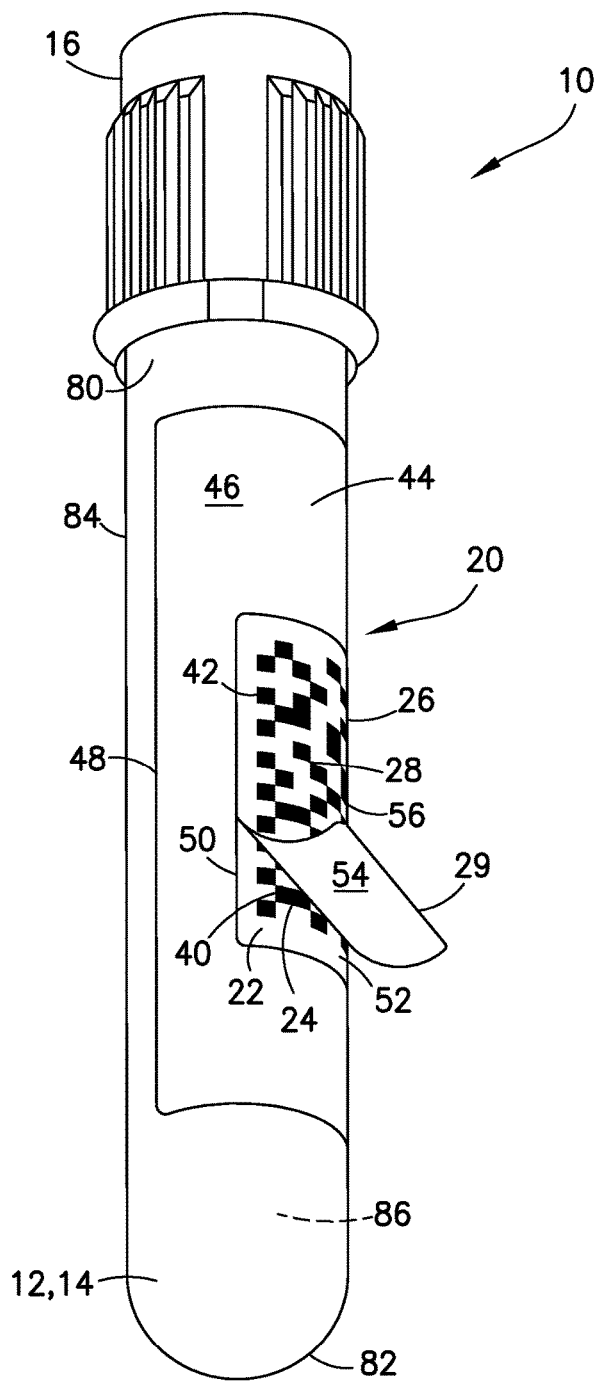
FIG. 1 is a perspective view of a biological sample containment system in accordance with an embodiment of the present invention.

The following description is provided to enable those skilled in the art to make and use the described embodiments contemplated for carrying out the invention. Various modifications, equivalents, variations, and alternatives, however, will remain readily apparent to those skilled in the art. Any and all such modifications, variations, equivalents, and alternatives are intended to fall within the spirit and scope of the present invention.

For purposes of the description hereinafter, the terms "upper", "lower", "right", "left", "vertical", "horizontal", "top", "bottom", "lateral", "longitudinal", and derivatives thereof shall relate to the invention as it is oriented in the drawing figures. However, it is to be understood that the invention may assume alternative variations and step sequences, except where expressly specified to the contrary. It is also to be understood that the specific devices and processes illustrated in the attached drawings, and described in the following specification, are simply exemplary embodiments of the invention. Hence, specific dimensions and other physical characteristics related to the embodiments disclosed herein are not to be considered as limiting.

Figure 2:
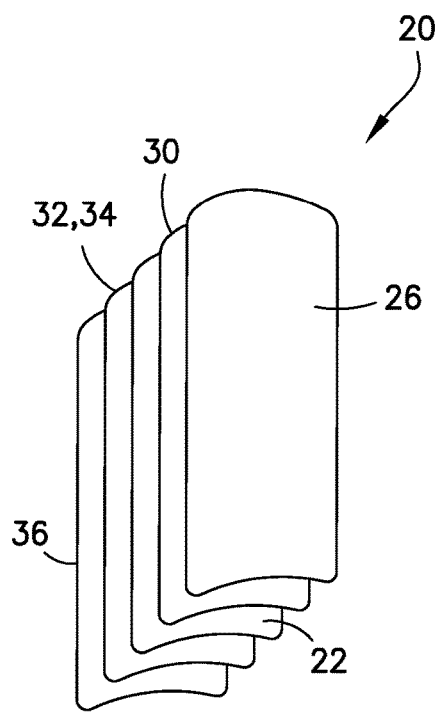
FIG. 2 is an exploded view of a labeling system in accordance with an embodiment of the present invention.

FIGS. 1 and 2 illustrate an exemplary embodiment of the present disclosure. Referring to FIGS. 1 and 2, a biological sample containment system 10 of the present disclosure includes a biological specimen collection container 12 for collecting a biological sample and a labeling system or label 20 for the container 12. In one embodiment, the label 20 includes a first layer 22 having a first readable information portion 24 and a second layer 26 removably attached to the first layer 22, the second layer 26 having a second readable information portion 28. In one embodiment, the first layer 22 and the second layer 26 of the label 20 are both formed of a thermosensitive material. In another embodiment, at least a portion of the first layer 22 and at least a portion of the second layer 26 are formed of a thermo-sensitive material. In one embodiment, at least a part of the first readable information portion 24 is identical to at least a part of the second readable information portion 28. The label 20 of the present disclosure allows a portion of the label 20 having readable information to be removed and adhered, such as by an adhesive on the label 20, to a patient record, for example, while a portion of the label 20 having identical readable information remains on the container 12.

Referring to FIGS. 1 and 2-6, a biological specimen collection container 12 for collecting a biological sample of the present disclosure is illustrated. In one embodiment, the container 12 comprises a specimen collection tube 14 and a closure 16. The specimen collection tube 14 may comprise any sample collection tubes or containers. For example, the specimen collection tube 14 may comprise a blood collection tube, a chemistry sample tube, a coagulation sample tube, a hematology sample tube, or other sample tube. In one embodiment, the tube 14 is generally cylindrical and may be made of one or more of the following representative materials: polypropylene, polyethylene terapthalate (PET), glass, or combinations thereof. In other embodiments, the biological specimen collection container 12 may comprise a vessel of a different shape, i.e., other than a cylindrical shape, and, in some instances, may not be a tube. For example, the biological specimen collection container 12 may comprise a collection cup, bag, or other container. In one embodiment, the closure 16 may be made of a resealable elastomeric polymer and additionally may comprise a polymer cap integral to the resealable elastomeric polymer.

The biological specimen collection container 12 may include an open top end 80, a closed bottom end 82, and a sidewall 84 extending therebetween, defining a container interior 86 adapted to receive a biological specimen, such as blood, therein. The closure 16 may cover the open top end 80 of the specimen collection container 12. In some embodiments, the specimen collection container 12 may be a single walled container formed of glass and/or a polymeric composition. In other embodiments, the specimen collection container 12 may include a tube-in-tube configuration in which a second specimen collection container is disposed within the container interior 86.

Referring to FIGS. 1 and 2, the biological sample containment system 10 of the present disclosure includes a labeling system or label 20 for the container 12. In one embodiment, the label 20 includes a first layer 22 having a first readable information portion 24 and a second layer 26 removably attached to the first layer 22, the second layer 26 having a second readable information portion 28. In one embodiment, at least a part of the first readable information portion 24 is identical to at least a part of the second readable information portion 28. The label 20 of the present disclosure allows a portion of the label 20 having readable information to be removed and adhered to a patient record, for example, while a portion of the label 20 having identical readable information remains on the container 12. The label 20 includes an additional identifying information portion 44 that has a front surface 46 and a rear surface 48. The first layer 22 includes a rear surface 50 and a front surface 52. The second layer 26 includes a rear surface 54 and a front surface 56. In one embodiment, the second layer 26 includes a flap 29 for easy gripping to facilitate removal of the second layer 26 from the first layer 22.

Referring to FIG. 2, the label 20 that can be applied to a container 12 includes multiple layers. For example, the label 20 includes a first layer 22, a second layer 26, a release layer 30, a securement portion 32, and a label backing 36.

The release layer 30 is disposed between the first layer 22 and the second layer 26. In this manner, the second layer 26 is removably attached to the first layer 22 such that the second layer 26 can be pulled off the first layer 22 and adhered to an item such as a patient record. In one embodiment, the release layer 30 comprises a weaker adhesive that allows the second layer 26 to be removably attached to the first layer 22.

In one embodiment, the label 20 includes a securement portion 32 on a surface of the first layer 22. For example, the securement portion 32 may be located on a rear surface 50 of the first layer 22. In one embodiment, the securement portion 32 comprises a stronger adhesive layer or adhesive 34 that allows the label 20 to be securely attached to a container 12. The label 20 also includes a label backing 36 disposed behind the securement portion 32 to cover and protect the securement portion 32 until it is desired to adhere the label 20 to a container 12. Before applying the label 20, the label backing 36 is removed and the securement portion 32 is adhered to a container 12.

In one embodiment, the first layer 22 and the second layer 26 of the label 20 are both formed of a thermosensitive material. The thermosensitive material may comprise any suitable material which allows for an image or indicia to be formed thereon or therein in response to an applied increase of temperature, such as, for example, a barcode burned therein. In one embodiment, the first layer 22 and the second layer 26 are formed of the same thermosensitive material.

The label 20 includes a first layer 22 having a first readable information portion 24 and a second layer 26 removably attached to the first layer 22, the second layer 26 having a second readable information portion 28. In one embodiment, at least a part of the first readable information portion 24 is identical to at least a part of the second readable information portion 28. The label 20 of the present disclosure allows a portion of the label 20 having readable information to be removed and adhered to a patient record, for example, while a portion of the label 20 having identical readable information remains on the container 12.

The first readable information portion 24 and/or the second readable information portion 28 of the label 20 may include any information identifying characteristics of the sample and/or container that may be useful to the healthcare practitioner. For example, the information may identify the integrity of the sample, whether the sample has been subjected to appropriate procedures, or whether the appropriate amount of sample has been collected.

Furthermore, the information may relate to maximum temperatures that the container and/or sample may be exposed to, the timeframe that the container and/or sample may be used upon manufacture, shipment, or some other event, or the amount of time that has transpired after collection of the sample into the container.

For example, the first readable information portion 24 and/or the second readable information portion 28 of the label 20 may include fill range indicators, low fill indicators, high fill indicators, hemolysis indicators, time indicators, temperature indicators, or other information identifying characteristics of the sample and/or container that may be useful to the healthcare practitioner.

In one embodiment, at least a part of the first readable information portion 24 is a first barcode 40 and at least a part of the second readable information portion 28 is a second barcode 42. In one embodiment, the second barcode 42 may be identical to the first barcode 40. In one embodiment, at least a part of the first readable information portion 24 and at least a part of the second readable information portion 28 comprise electronically readable information.

For example, in one embodiment, included on a portion of the label 20 is a barcode or some other machine readable data that is unique to each container or optionally unique to a subset of containers. Such information may also be used for storage of additional data associated with a container, such as container manufacturer information, container type, intended draw size information, and the like. In addition, patient-specific, test-specific, or other application-specific information may be stored, e.g., electronically, and associated with the container's unique identifier.

The first readable information portion 24 and/or the second readable information portion 28 of the label 20 may include a radio frequency identification (RFID) tag which provides information associated with a container. An RFID tag allows for unique identification of the container. Such RFID tags may be passive in nature with an electronic device having some type of reading/scanning mechanism to receive identification information off the tag. In another embodiment, the tag is active in nature in which an electronic device is used to receive a signal generated by or from the tag. In accordance with an embodiment of the invention, the tags may be writeable, readable, or both. With such a system, the need for more conventional type labeling having machine readable or human readable information may be complemented or obviated.

The first readable information portion 24 and/or the second readable information portion 28 of the label 20 may include information relating to monitoring the maximum temperature to which the label 20 and the container 12 are exposed. In another embodiment, the label 20 may include information relating to measuring the temperature once the label 20 and the container 12 are exposed to light and/or air.

The first readable information portion 24 and/or the second readable information portion 28 of the label 20 may include information relating to a time and temperature shelf life indicator that allows a user to easily observe whether a container has "expired" prior to drawing a sample, testing the sample, or some other point in the sample collection and testing process resulting in fewer redraws or unnecessary or inaccurate testing.

Referring to FIGS. 1-6, the first readable information portion 24 and/or the second readable information portion 28 of the label 20 may include information relating to a mix indicator 90 that ensures that the appropriate number of mixes and amount of mixing time is performed. Adequate mixing improves sample integrity, quality, and reliability. In one embodiment, an accelerometer may be integrated with the container 12 such that motion representative of mixing may be identified, recorded, and outputted. The output may be in a form that is visually apparent to the user or optionally may be discreet such that the output may be interrogated by a device remote from the tube, i.e., a reading from a hand-held scanner.

Referring to FIGS. 1-6, the first readable information portion 24 and/or the second readable information portion 28 of the label 20 may include information relating to a hemolysis indicator, possibly in the form of a chart or scale. One method for measuring levels of hemolysis, i.e., the breaking of the cell membranes of red blood cells, is visually identifying the color of all or a portion of a blood sample. For example, in many instances, the shade of the serum that resides above the hematocrit for a blood sample is indicative of general qualitative hemolysis levels, such as zero, trace (or slight), moderate, and gross (or severe). Such indication may be displayed by including a color scale on a blood containment device having different hemolysis level terminologies associated with and printed on the hemolysis scale. Some examples of scales/terminologies that can be included to convey for measuring levels of hemolysis are: a 0, +1, +2, and +3 scale; a 0, 1+, 2+, and 3+ scale; a 0, 1, 2, and 3 scale; a 0, +, ++, and +++ scale; or a zero, trace, +, ++, and +++ scale. The color scale for indicating hemolysis ranges from a light yellow to a dark reddish orange. A Pantome color scheme may be chosen to represent variances between the low and high color indicators. Other indications of hemolysis levels may be provided.

Referring to FIGS. 1, 2, 5, and 6, the label 20 includes an additional identifying information portion 44 that has a front surface 46 and a rear surface 48. The first layer 22 includes a rear surface 50 and a front surface 52. The second layer 26 includes a rear surface 54 and a front surface 56. Referring to FIG. 6, in one embodiment, the rear surface 48 of the additional identifying information portion 44 and/or the rear surface 50 of the first layer 22 includes a first information area 91, a second information area 92, a third information area 94, a fourth information area 96, and a fifth information area 98. The information areas may include any of the identifying information described above. In other embodiments, the rear surface 48 of the additional identifying information portion 44 and/or the rear surface 50 of the first layer 22 may include any orientation and/or number of information areas configured to provide any of the identifying information described above.

In one embodiment, the rear surface 48 of the additional identifying information portion 44 and/or the rear surface 50 of the first layer 22 may include information pertaining to at least one of a manufacture catalog number, identifiable bar code, shelf life, lot identification number, container specific identifier, information specific to a sample intended to be placed or already placed into the container, and/or information specific to a patient in a hospital.

FIGS. 3 and 4 illustrate another exemplary embodiment. The embodiment illustrated in FIGS. 3 and 4 includes similar components to the embodiment illustrated in FIGS. 1, 2, 5, and 6, and the similar components are denoted by a reference number followed by the letter A. For the sake of brevity, these similar components and the similar steps of using a biological sample containment system 10A (FIGS. 3 and 4) will not all be discussed in conjunction with the embodiment illustrated in FIGS. 3 and 4.

Referring to FIGS. 3 and 4, the biological sample containment system 10A includes a label 20A for a container 12A that includes a fill line indicator 60. In one embodiment, the fill line indicator 60 may comprise some form of pre-printed marking or shape specific marking, such as a black solid indicator portion or a cut, cutout, or visible perforation portion. The color, shading, pattern, and shape of such portions may vary as long as each is recognizable by the user. In one embodiment, the fill line indicator 60 includes a low fill indicator situated at the bottom boundary of the fill line indicator 60 and a high fill indicator situated at the upper boundary of the fill line indicator 60. In other embodiments, one of either a low fill indicator or high fill indicator may be utilized. The low fill indicator and the high fill indicator set the lower and upper limits for drawing a sample from a sample source, e.g., a patient's venous blood, such that sufficient sample amounts are collected to effectuate certain tests and to effectuate adequate reagent to sample mixing ratios and proper centrifugation considerations or conditions. In another embodiment, the word "fill" or some other word indicative of the indicator's purpose may be displayed in the indicator area. High fill, low fill, and generic fill indicators may comprise boundaries of each limit, or optionally may include a filled or empty space area correlating to a desired fill range. For certain containers, the desired fill range may correlate to the quantity of reagents or additives deployed into the container prior to use or at the point of manufacture to ensure proper sample to additive ration. The fill line indicators may be disposed on a portion of the label 20 such that a user may interpret the level or quantity of sample collected from the patient into the container by looking through a portion of the generally clear sidewall of the container 12.

In one embodiment, a portion of the first layer 22A includes the fill line indicator 60. For example, referring to FIG. 4, the first layer 22A includes a notch 64 that can be used as the fill line indicator 60.

In one embodiment, a portion of the second layer 26A includes the fill line indicator 60. For example, referring to FIG. 3, the second layer 26A includes a band 62 that can be used as the fill line indicator 60.

Figure 7:
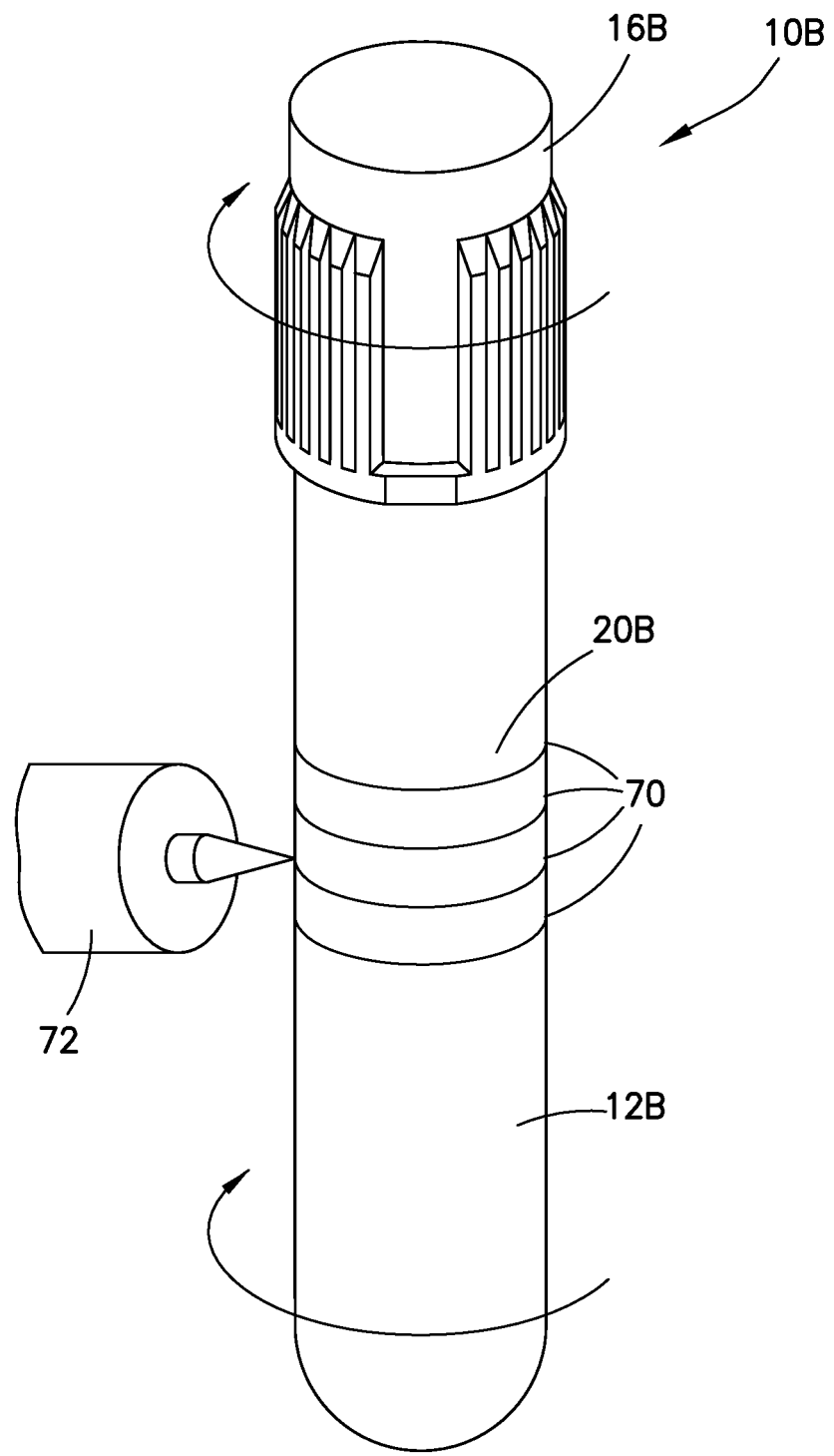
FIG. 7 is a perspective view of a biological sample containment system and a reading needle in accordance with another embodiment of the present invention.
Figure 8:
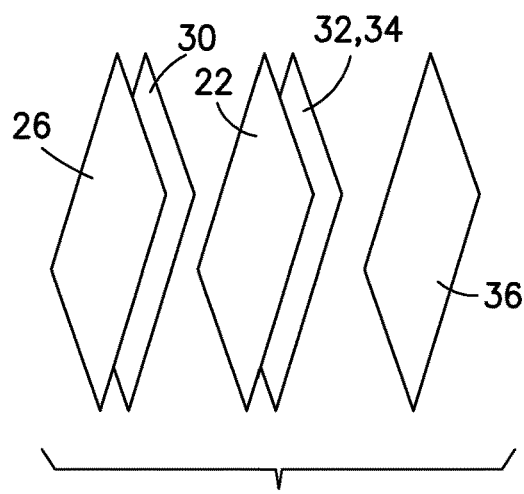
FIG. 8 is an exploded view of a labeling system in accordance with an embodiment of the present invention.

FIG. 7 illustrates another exemplary embodiment. The embodiment illustrated in FIG. 7 also includes similar components to the embodiment illustrated in FIGS. 1, 2, 5, and 6, and the similar components are denoted by a reference number followed by the letter B. For the sake of brevity, these similar components and the similar steps of using a biological sample containment system 10B (FIG. 7) will not all be discussed in conjunction with the embodiment illustrated in FIG. 7.

Referring to FIG. 7, the biological sample containment system 10B includes grooves 70 disposed in a label 20B or a container 12B and a reading needle 72. In such an embodiment, information may be obtained using the reading needle 72 which can be disposed within the grooves 70 while the container 12B is rotated as shown in FIG. 7.

Figure 9:
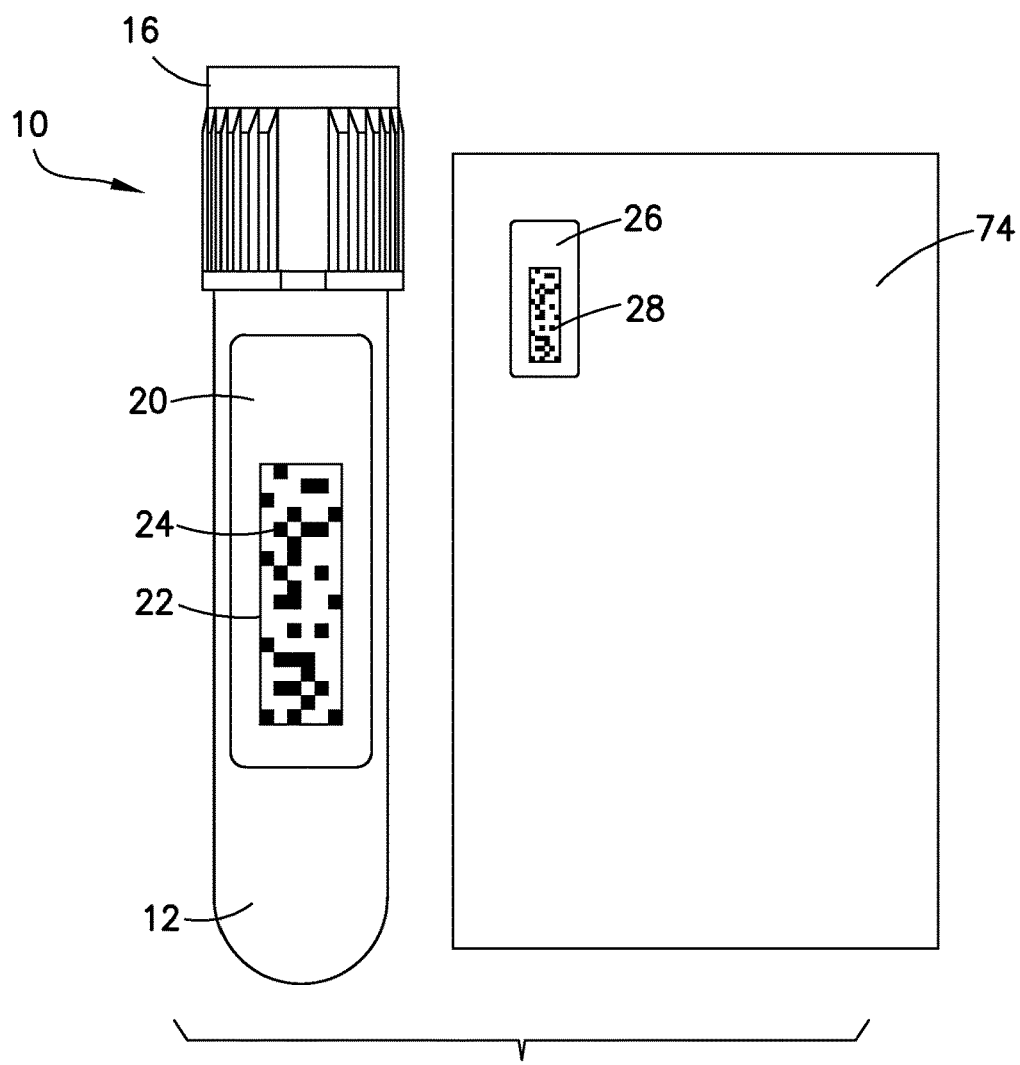
FIG. 9 is a front view of a biological sample containment system having a first layer of a label on a container and a second layer of the label on a patient record in accordance with an embodiment of the present invention.

Referring to FIG. 9, as described above, the label 20 of the present disclosure allows a second layer 26 of the label 20 having readable information 28 to be removed and adhered to a patient record 74, for example, while a first layer 22 of the label 20 having identical readable information 24 remains on the container 12.

Figures 11, 12:
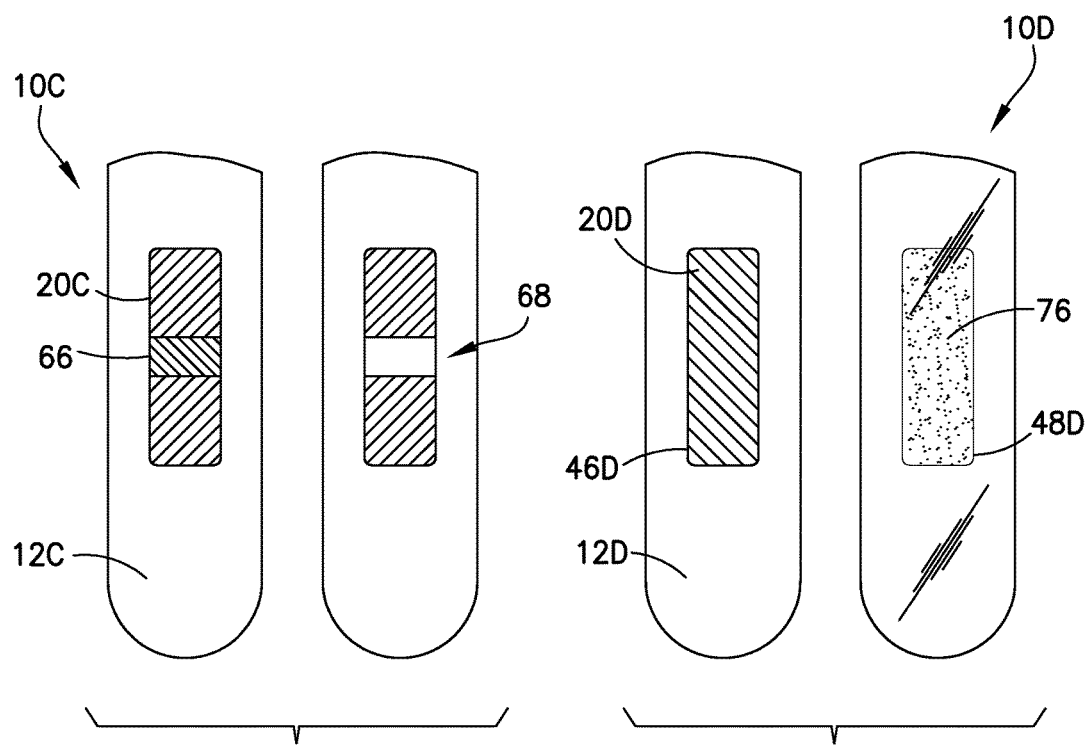
FIG. 11 is elevation views of a biological sample containment system in accordance with another embodiment of the present invention.
FIG. 12 is elevation views of a biological sample containment system in accordance with another embodiment of the present invention.

FIGS. 11 and 12 illustrates other exemplary embodiments. The embodiment illustrated in FIGS. 11 and 12 includes similar components to the embodiment illustrated in FIGS. 1, 2, 5, and 6, and the similar components are denoted by a reference number followed by the letters C and D. For the sake of brevity, these similar components and the similar steps of using a biological sample containment system 10C (FIG. 11) and a biological sample containment system 10D (FIG. 12) will not all be discussed in conjunction with the embodiment illustrated in FIGS. 11 and 12.

Referring to FIG. 11, the biological sample containment system 10C includes a label 20C for a container 12C that includes a tear away portion 66. In such an embodiment, the tear away portion 66 may be removed so that a fill line indicator or clear portion 68 is exposed.

Referring to FIG. 12, the biological sample containment system 10D includes a label 20D for a container 12D that includes an invisible bar code label 76 on a rear surface 48D of the label 20D. In such an embodiment, a camera recognition system may be used with the invisible bar code label 76 to read and utilize information.

Referring to FIGS. 1-10, a method of providing information on a container will now be described. The method includes providing a label 20 having a first layer 22 formed of a thermosensitive material and a second layer 26 removably attached to the first layer 22 and formed of a thermosensitive material; providing a container 12; adhering the label 20 to the container 12; and imparting a first readable information portion 24 in the first layer 22 and a second readable information portion 28 in the second layer 26. In one embodiment, the method includes simultaneously imparting the first readable information portion 24 in the first layer 22 and the second readable information portion 28 in the second layer 26.

Figure 10:
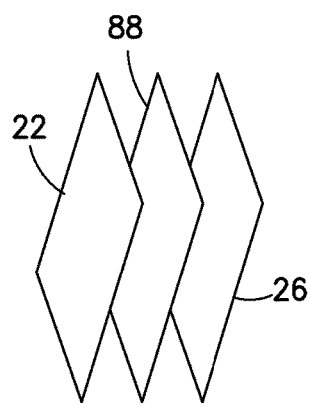
FIG. 10 is an exploded view of a labeling system in accordance with another embodiment of the present invention.

In one embodiment, the label 20 of the present disclosure is capable of receiving information so that the label 20 may first be secured to a container 12 and then the information may be imparted into the first layer 22 and the second layer 26 after the label 20 is secured to a container 12. In one embodiment, the first layer 22 and the second layer 26 are formed of a thermosensitive material to allow information to be burned into the first layer 22 and the second layer 26. In one embodiment, the first layer 22 and the second layer 26 include preprinted information and other information may be imparted to the first layer 22 and the second layer 26 after securing the label 20 to a container 12. In one embodiment, a thermal energy source may be used to impart information to the label 20. Referring to FIG. 10, in one embodiment, thermal ink 88 may be used to print information and/or a barcode onto a first layer 22 and/or a second layer 26 of the label 20.

While this disclosure has been described as having exemplary designs, the present disclosure can be further modified within the spirit and scope of this disclosure. This application is therefore intended to cover any variations, uses, or adaptations of the disclosure using its general principles. Further, this application is intended to cover such departures from the present disclosure as come within known or customary practice in the art to which this disclosure pertains and which fall within the limits of the appended claims.

What is claimed is:

1. A label for a container, the label comprising:
a first layer having a first readable information portion, at least a portion of the first layer formed of a thermosensitive material having first readable information burned thereon or therein;
an adhesive layer located on a back surface of the first layer and a release layer comprising an adhesive located on a front surface of the first layer, said front surface being an opposite surface from the back surface, said adhesive layer capable of securely adhering the label to the container; and
a second layer having a back surface superimposed on and removably secured to a portion of the release layer and a portion of the first layer, the second layer having a second readable information portion having a second readable information which is identical to the first readable information burned therein or thereon, at least a portion of the second layer formed of a thermosensitive material, wherein the first and second layers are arranged with respect to each other such that the first and second readable information are simultaneously formed on or in the first and second layers in response to an application of heat at a predetermined temperature, and wherein the release layer enables the second layer to be removed from the first layer.

2. The label of claim 1, further comprising a fill line indicator.

3. The label of claim 2, wherein a portion of the first layer includes the fill line indicator.

4. The label of claim 2, wherein a portion of the second layer includes the fill line indicator.

5. The label of claim 1, wherein the first layer and the second layer are formed of the same thermosensitive material.

6. A biological sample containment system, comprising:
a container for collecting a biological sample; and
a label for the container, the label comprising:
a first layer having a first readable information portion and formed of a thermosensitive material having first readable information burned thereon or therein, the first layer including an adhesive layer located on a back surface positioned adjacent to and adhered to the container;
a second layer having a back surface superimposed on and removably attached to a front surface of the first layer, the second layer having a second readable information portion having a second readable information which is identical to the first readable information burned therein or thereon and formed of a thermosensitive material, and wherein the first and second layers are arranged with respect to each other such that the first and second readable information are simultaneously formed on or in the first and second layers in response to an application of heat at a predetermined temperature; and
a release layer disposed between the first layer and the second layer, wherein the release layer facilitates the removal of the second layer from the first layer.

7. The biological sample containment system of claim 6, wherein the label further comprises a fill line indicator.

8. The biological sample containment system of claim 7, wherein a portion of the first layer includes the fill line indicator.

9. The biological sample containment system of claim 7, wherein a portion of the second layer includes the fill line indicator.

10. The biological sample containment system of claim 6, wherein the first layer and the second layer are formed of the same thermosensitive material.

11. The biological sample containment system of claim 6, wherein the container is a biological specimen collection container.

12. The biological sample containment system of claim 6, wherein the container is a blood collection tube.

13. The biological sample containment system of claim 6, wherein the second layer is capable of being removed from the container and adhered to another surface while the first layer, having identical readable information as the second layer, remains on the container.

14. The biological sample containment system of claim 6, wherein the first and second readable information is capable of being imparted into the first layer and the second layer after the label is secured to the container.

15. A biological sample containment system, comprising:
a container for collecting a biological sample; and
a label for the container, the label comprising:
a first layer having a first readable information portion and formed of a thermosensitive material having indicia formed thereon in response to an application of increased temperature, the first layer including an adhesive layer located on a back surface positioned adjacent to and adhered to the container;
a second layer having a back surface superimposed on and removably attached to a front surface of the first layer, the second layer having a second readable information portion identical to at least a part of the first readable information portion and formed of a thermosensitive material having indicia formed thereon in response to the application of increased temperature; and
a release layer disposed between the first layer and the second layer, wherein the release layer facilitates the removal of the second layer from the first layer,
wherein the first readable information portion and the second readable information portions are superimposed on one another such that the first and the second readable information are simultaneously formed on the first and second layers in response to the application of heat.

16. The biological sample containment system of claim 15, wherein the label further comprises a fill line indicator.

17. The biological sample containment system of claim 16, wherein a portion of the first layer includes the fill line indicator.

18. The biological sample containment system of claim 16, wherein a portion of the second layer includes the fill line indicator.

19. The biological sample containment system of claim 15, wherein the container is a biological specimen collection container.

20. The biological sample containment system of claim 15, wherein the container is a blood collection tube.

* * * * *